United States Patent [19]
Schmidt et al.

[11] Patent Number: 5,545,463
[45] Date of Patent: Aug. 13, 1996

[54] HEEL/METATARSAL STRUCTURE HAVING PREMOLDED BULGES

[75] Inventors: Karl M. Schmidt, Woodside; Michelle R. Schmidt, Palo Alto; George S. Cole, Pebble Beach; Stuart E. Jenkins, Thousand Oaks, all of Calif.; Harry W. Edwards, Barrington, Ill.

[73] Assignee: Energaire Corporation, Pebble Beach, Calif.

[21] Appl. No.: 398,919

[22] Filed: Mar. 6, 1995

Related U.S. Application Data

[63] Continuation-in-part of Ser. No. 993,099, Dec. 18, 1992, Pat. No. 5,395,674.

[51] Int. Cl.$^6$ .............................. B32B 1/00; A43B 13/20
[52] U.S. Cl. ........................ 428/178; 428/72; 428/174; 428/212; 428/908.8; 36/29; 36/35 B
[58] Field of Search ...................... 428/156, 178, 428/174, 72, 212, 908.8; 36/29, 35 R, 35 B

[56] References Cited

U.S. PATENT DOCUMENTS

| | | | |
|---|---|---|---|
| 745,793 | 12/1903 | Corman | 36/35 |
| 1,977,695 | 10/1934 | Pinaud | 36/25 R |
| 2,532,742 | 12/1950 | Stoiner | 36/35 |
| 3,044,190 | 7/1962 | Urbany | 36/29 |
| 4,071,963 | 2/1978 | Fukuoka | 36/3 B |
| 4,224,749 | 9/1980 | Diaz-Cano | 36/38 R |
| 4,358,902 | 11/1982 | Cole et al. | 36/28 |
| 5,395,674 | 3/1995 | Schmidt et al. | 428/178 |

FOREIGN PATENT DOCUMENTS

| | | |
|---|---|---|
| 871261 | 7/1951 | Germany. |
| 1287477 | 1/1969 | Germany. |

*Primary Examiner*—Donald Loney
*Attorney, Agent, or Firm*—Emrich & Dithmar

[57] ABSTRACT

A plurality of bulges is molded into the heel portion or metatarsal portion of the bottom member of a shoe, the bulges respectively defining cavities. At least one restricted passageway is molded into the portion between the cavities. A sealing member is attached to the outer member by adhesive, whereby air at atmospheric pressure is permanently located in the space jointly defined by the passageway and the cavities.

8 Claims, 9 Drawing Sheets

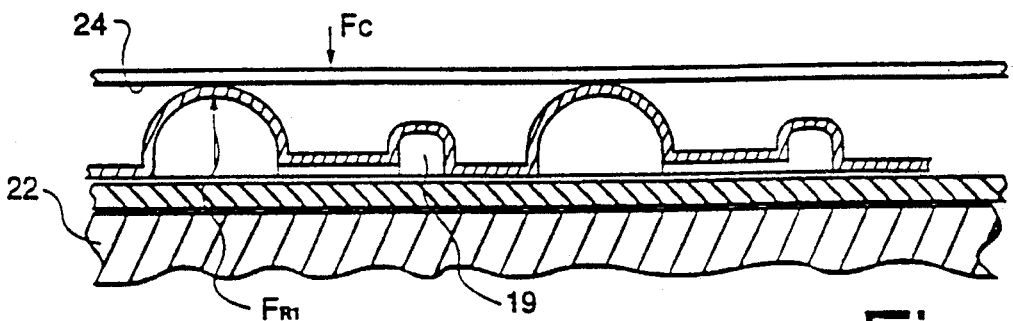
Fig. 2a
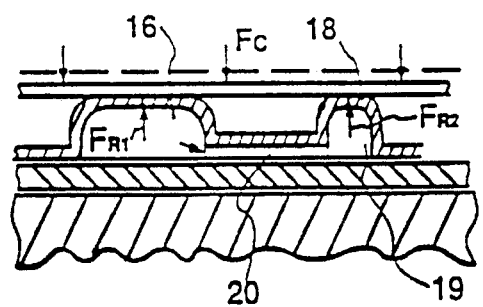
Fig. 2b
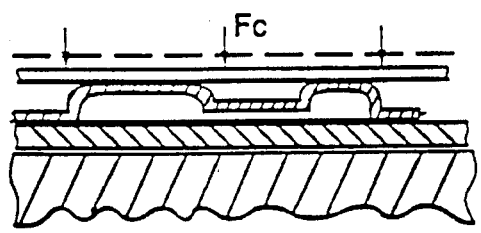
Fig. 2c
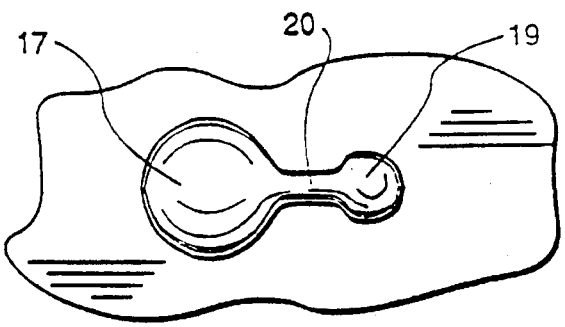
PLAN VIEW Fig. 2d

HEEL/METATARSAL STRUCTURE HAVING PREMOLDED BULGES

CROSS-REFERENCE TO RELATED APPLICATION

This is a continuation-in-part of U.S. application Ser. No. 07/993,099, filed Dec. 18, 1992, now U.S. Pat. No. 5,395,674 issued Mar. 7, 1995.

BACKGROUND OF THE INVENTION

U.S. Pat. No. 4,577,417, assigned to the same assignee as the present application, discloses a sole-and-heel structure having a premolded bulge under-the heel region, a premolded bulge under the metatarsal region and a passageway between the two bulges. Air in the cavities defined by the two bulges moves back and forth in the passageway.

The present invention involves premolded bulges in the heel portion only which bulges are connected by one or more passageways, or premolded bulges in the metatarsal portion only connected by one or more passageways, or passageway connected premolded bulges in both the heel portion and in the metatarsal portion, but without passageways between the bulges in the two portions.

SUMMARY OF THE INVENTION

In summary, there is provided a molded, one-piece resilient outer member having a heel portion and/or a metatarsal portion, the outer member having interior and exterior surfaces and having a construction to be highly wear resistant to enable said exterior surface to contact a support surface during use, a plurality of bulges molded into one of the portions and projecting from the exterior surface, the bulges respectively defining cavities opening at the interior surface, the bulges projecting from the exterior surface without the application of any elevated fluid pressure in the cavities, at least one restricted passageway molded into-the outer member between the cavities and opening to the interior surface, a sealing member having a shape that matches the shape of the outer member, the sealing member being impermeable to air and having a sealing surface, and adhesive means between the sealing surface and the interior surface for hermetically attaching the sealing member to the outer member, whereby air at atmospheric pressure is permanently located in the space jointly defined by the passageway and the cavities, there being no passageways between the cavities and the other portion.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings preferred embodiments thereof, from an inspection of which, when considered in connection with the following description, the invention, its construction and operation, and many of its advantages should be readily understood and appreciated.

FIGS. 2a, 2b, and 2c are cross-sections taken along the line 2—2 of FIG. 1;

FIG. 2d is a plan view of one unit of FIG. 1;

DESCRIPTION OF THE PREFERRED EMBODIMENTS

Figure 1:
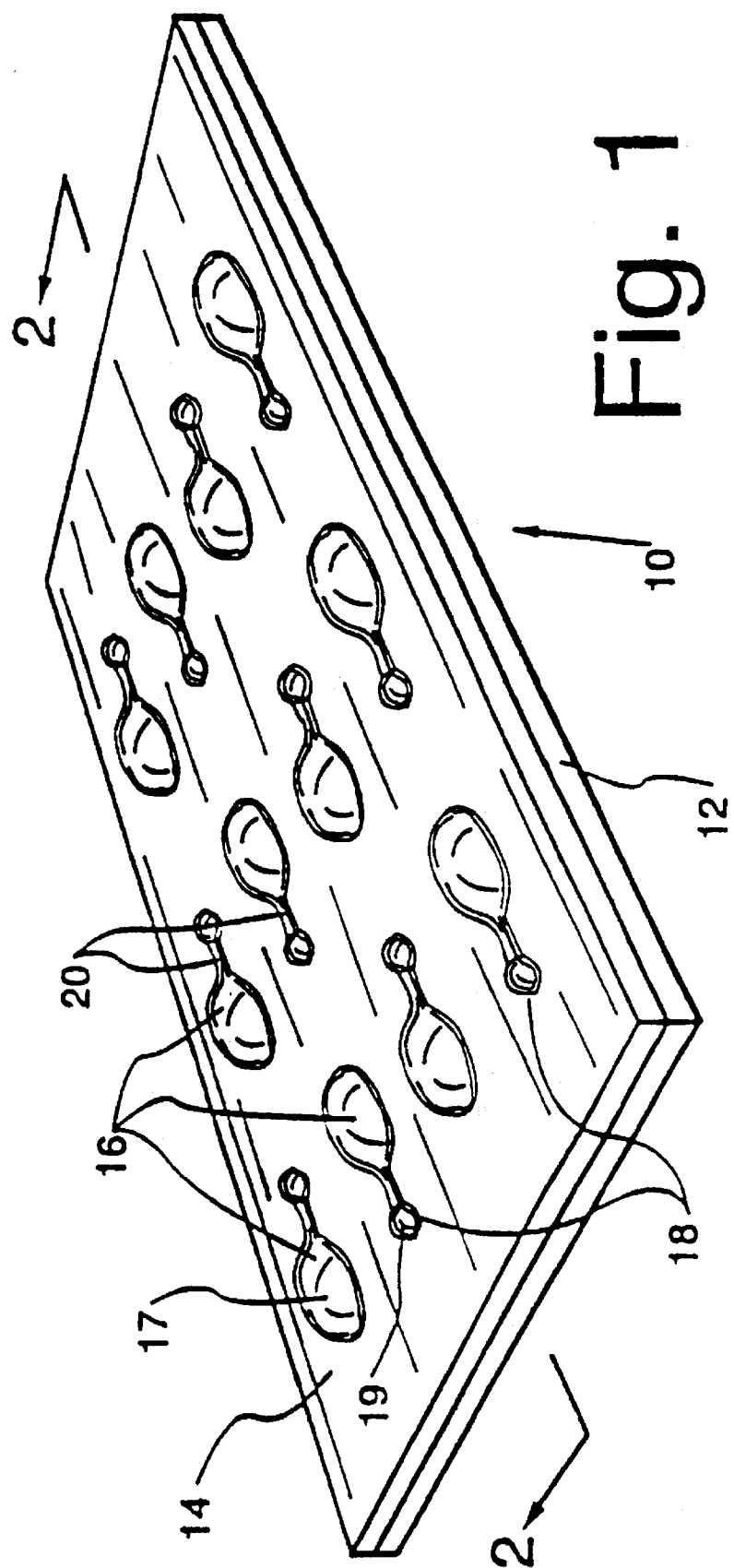
FIG. 1 is a perspective view of an air sheet having units of bulges interconnected by passageways.

Referring now to FIG. 1 of the drawings, a sheet of shock absorbing material 10 includes a flat or planar configured base sheet 12 overlaid by a top sheet 14 of resilient or elastic material deformed upwardly at regular intervals to define upwardly extending but downwardly open relatively large bubbles or bulges 16 forming cavities 17, and adjacent smaller bubbles or bulges 18 forming cavities 19, the two being joined together by a communicating passageway 20. The upper sheet 14 is glued or otherwise bonded to the lower base sheet 12 so as to close the cavities and form the relatively large cavities 17 in bulges 16 and the relatively small cavities 19 in smaller bulges 18. The cavities 17 and 19 of each large/small pair are intercommunicated by a passageway 20 which is closed on the lower side by the base 12. The cavity pairs are organized and oriented to achieve high density over the upper surface area of the pad.

Although the cavity sizes are depicted in FIG. 1 as large compared to the thickness of the sheet, it is to be understood that, depending on the intended application, the "large" cavities can range from small fractions of an inch in diameter to several inches in diameter. The dimensions of the smaller cavities would be scaled proportionally smaller. Similarly, the thickness of the sheet or sheets 12, 14 can, range from extremely thin membrane thicknesses to large thicknesses of several inches or more.

Referring now to FIG. 2a, which is a partial cross-sectional view taken along the line 2—2 of FIG. 1, it will be observed that if the pad is laid upon a planar supporting surface 22 and a compressive force $F_C$ is applied to the top of the pad by means a planar member 24, the larger bulges will be engaged and will initially resiliently resist the compression. However, as they are compressed, as depicted in FIG. 2b, the air or other fluid contained within the bulges 16 will be forced through passageways 20 into the smaller cavities 19 causing the bulges 18 to expand and rise up to be engaged by the surface 24. This is to say that as bulges 16 are collapsed they exert an upwardly directed resisting force $F_{R1}$ upon the surface 22. At this point, further downward movement of the member 24 will cause both bulges 16 and 18 to be resiliently collapsed, as depicted in FIG. 2c, with a second resisting force $F_{R2}$ being additionally exerted by the bulge 18 of each pair. It will thus be noted that the resilient resistance to compression is nonlinear and in fact tends to operate in step-like fashion as the sheet is compressed. That is, during the initial stage of compression the resisting force $F_{R1}$ is generated as the fluid within cavity 17 is compressed and as the smaller cavity 19 is expanded upwardly; during the second stage of compression, the two bulges 16 and 18 are simultaneously compressed and jointly exert a total resisting force $F_{RT}=F_{R1}+F_{R2}$, as the pad is driven to maximum compression as illustrated in FIG. 2c.

A plan view of a unit comprising a large bulge 16 and a small bulge 18 is illustrated in FIG. 2d.

Figure 3:
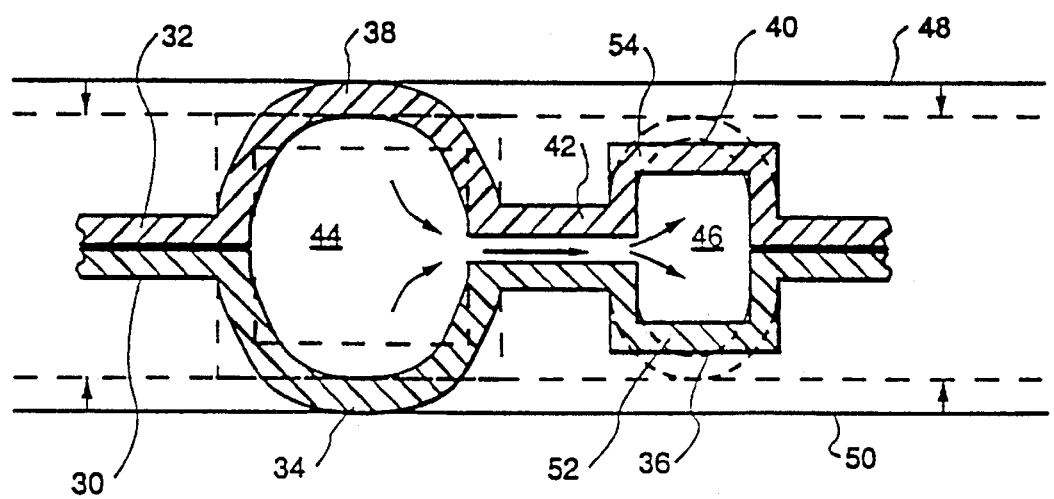
FIG. 3 is a cross-sectional view of alternative configuration.

FIG. 3 is a cross-sectional view taken through an alternative embodiment is depicted wherein the bottom layer of material 30, instead of being planar, is deformed to include downwardly extending bulges 34 and 36 in mirror-image correspondence to the bulges 38 and 40 of upper sheet 32 such that a greater volume of fluid may be contained within the respective cavities 44 and 46. At least one of the sheets is provided with passageways 42 for communicatively coupling the cavities 44 and 46.

In this configuration, as the larger bulges are collapsed by engagement between two members 48 and 50, the smaller bulges expand both upwardly and downwardly to engage the compressing surfaces and provide increased resilient resistance to compression. Whereas, the larger bulges 34 and 38 in the upper and lower sheets are generally hemispherical in configuration, the smaller bulges 36 and 40 are configured more pill-box in shape so to provide surfaces 52 and 54 which will readily expand upwardly and downwardly when subjected to increased internal pressure as would result from compression of the larger bulges 34, 38.

The smaller cavity 46 need not extend outwardly on both sides of the planes of the sheets 30 and 32. In some application it may be desirable that the small cavities distend in only one direction.

Figure 4:
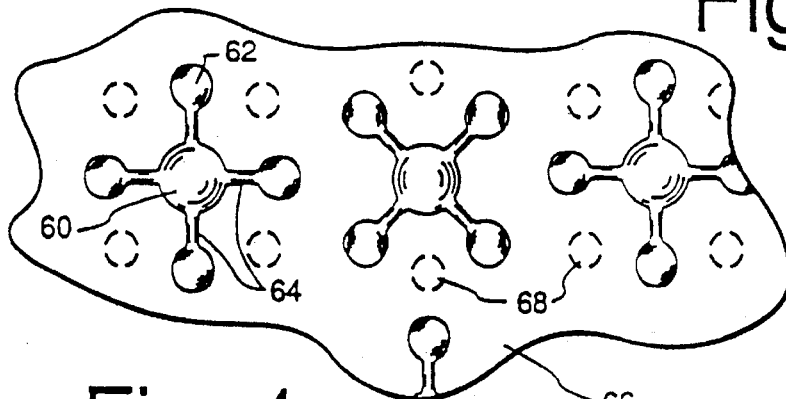
FIG. 4 is a plan view of an alternative configuration.

In FIG. 4, a plurality of larger central bulges 60 are each surrounded by an array of smaller satellite bulges 62 joined thereto by passageways 64. The large bulge/small bulge combinations, typically formed along the lines described above, are alternately rotated so as to provide a uniform distribution and high density of cavities across the surface of the material 66 forming the pad. In addition, for some applications it may be appropriate to add holes through the sheet material, as shown by the dotted circles 68, to allow air or liquid to pass through the pad from one side to the other.

Figure 5:
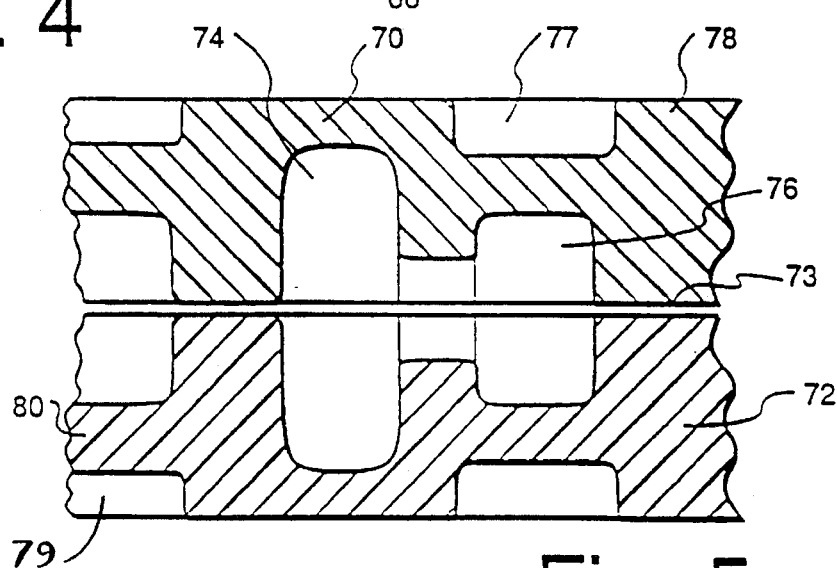
FIGS. 5 and 6 are cross-sectional views of alternative configurations.

In FIG. 5, two sheets of molded compressible material 70 and 72 are joined at 73 to form a substantially flat outer-surfaced pad. The large and small cavities 74 and 76, and the communicating passageways 73 are molded into the adjacent surfaces of the sheets 78 and 80, and small open cavities 77 and 79 are formed in the outer surfaces above the smaller cavities in order to allow such cavities to herniate outwardly to meet and engage the compressing surfaces.

Figure 6:
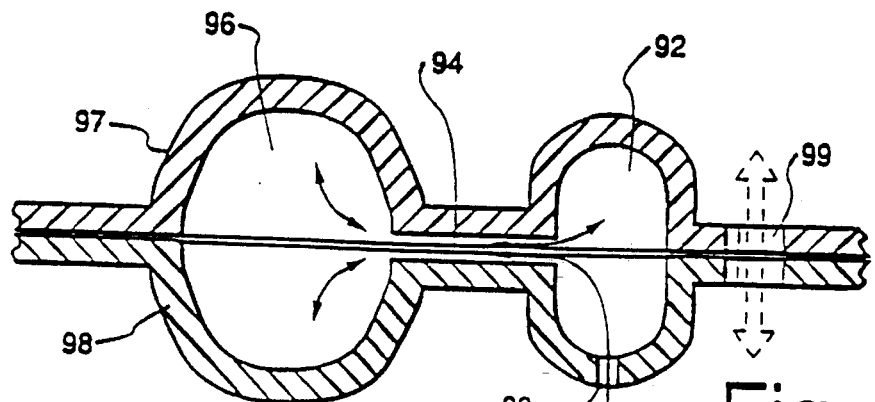

FIG. 6 depicts a cross-section similar to that of FIG. 3 and includes the addition of an opening 90 in one of the walls forming the small cavity 92 which, via passageway 94, is in communication with a larger cavity 96. In operation, compression of cavity 96 would force air out of passageway 94 and, assuming the materials forming the layers 97 and 98 are sufficiently resilient, removal of the compressive force would allow the materials to return to their undeformed state and cause the expelled air to return through the opening 90. By judicious selection of the size of the hole or holes 90, a throttling function can be effected to modify the damping rate of the shock-absorbing action. Holes 99 may be included to allow air or liquid to pass through the pad formed by the sheets 97 and 98.

Figure 7:
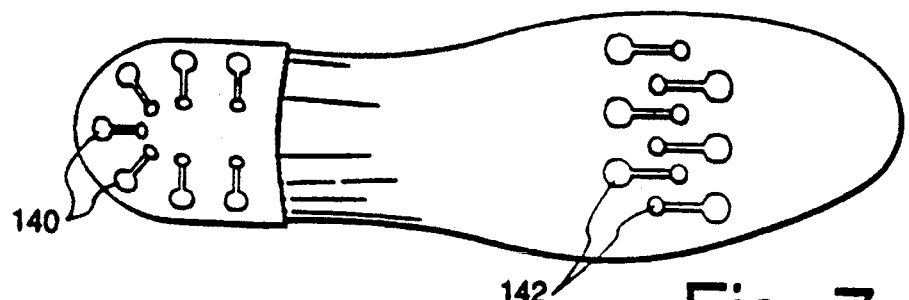
FIGS. 7, 8 and 9 illustrate the air sheet on shoe soles.
Figure 8:
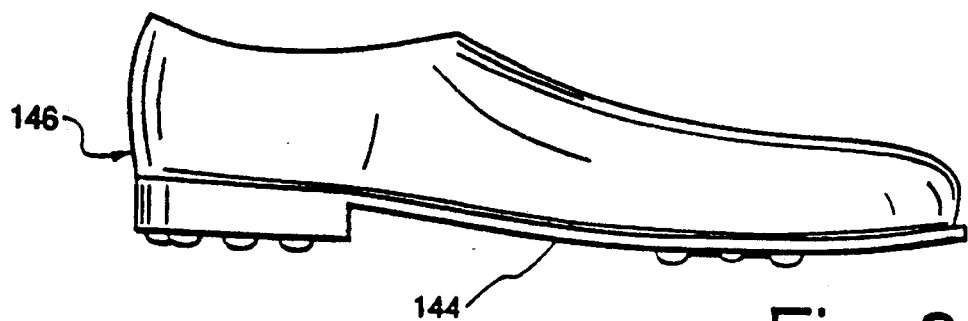

FIGS. 7 and 8 depict embodiments particularly suited for footwear applications. As illustrated, a plurality of the "pumping units" 140 and 142 of the type shown in FIGS. 1–6 are strategically positioned in the heel and metatarsal positions of the outer sole 144 of a shoe 146 to provide superior shock absorption. The large and small bulges act as studs adding to shoe traction while at the same time cushioning the forces applied to the shoe wearer's heel and the balls of his or her feet.

Figure 9:
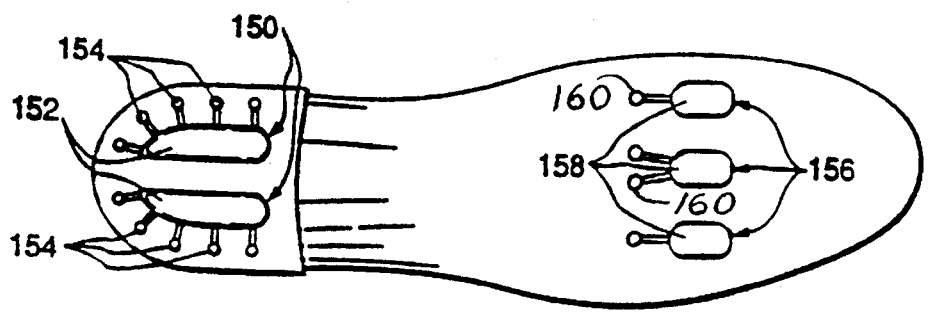

In FIG. 9, a plurality of pumping units is provided in the heel and metatarsal portions of a shoe. In the heel, two multiple small units 150 are provided. The larger bulges 152 are disposed on each side of the longitudinal centerline of the shoe and the smaller bulges 154 are arranged around the outer perimeter of the heel. These units will, in addition to their shock-absorbing function, serve to provide lateral stability to the heel. The metatarsal units 156 have their large bulges 158 positioned directly under the ball of the foot. The smaller bulges 160 are positioned rearwardly of the bulges 158 so as to provide a forward lift as they are inflated. Those skilled in the shoe art will readily appreciate that various combinations and arrays of the pumping units of the present invention can be used in footwear to add stability and to correct supination and pronation problems.

The multi-cavitied configurations depicted in the drawing and described hereinabove form small pumping mechanisms which actively resist the collapse or compression of the sheet or other shaped material in which they are formed. The basic principle of the miniature pumps is that air or other fluid trapped in the larger ball-shaped cavities, which in most embodiments protrude from the plane of the sheet, when compressed, will pass the compressed fluid through a narrow passageway to a smaller cavity which then expands to meet a compressing surface and add its resisting force to counter the compressing action. By way of example, should a weight be dropped upon a pad of the type depicted in FIGS. 1 and 2, there will be a decelerating effect at a first rate as the weight compresses the larger cavities, forcing fluid into the smaller cavities which expand, rising to meet the weight. As the weight meets the expanded smaller cavities, and tends to compress them along with the larger cavities, the weight will be caused to decelerate at a second rate, etc. Accordingly, the functionality of the present invention differs materially from prior art resilient pads, bubble packs and the like.

Figure 10:
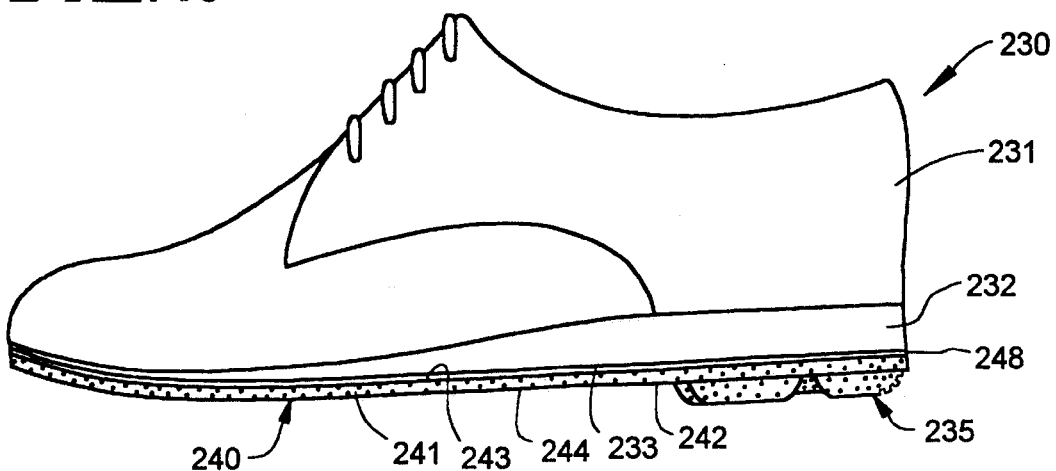
FIG. 10 is a side elevational view of a shoe embodying heel structure incorporating the features of the present invention.

Turning to FIG. 10, there is depicted a shoe 230 having a conventional upper portion or last 231 and a so-called mid-sole 232 which is generally of wedge shape, whereby the shoe 230 is referred to as being of the "wedge-type." The sole 232 has a downwardly facing surface 233.

Figure 11:
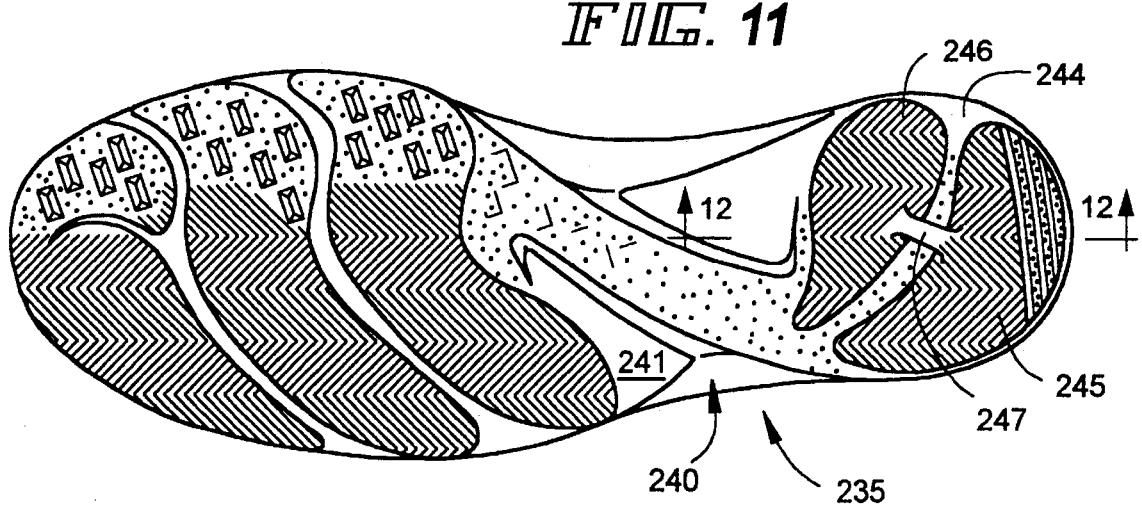
FIG. 11 is a bottom plan view of the shoe of FIG. 10 on an enlarged scale.
Figure 12:
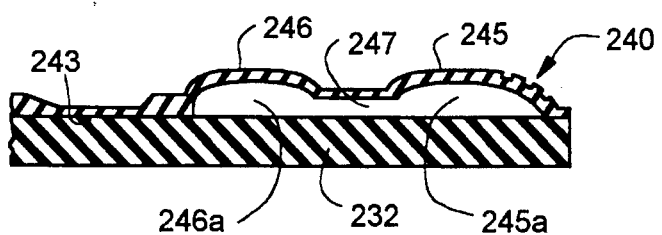
FIG. 12 is a fragmentary view taken in longitudinal section of the heel structure, along the line 12—12 of FIG. 11, on an enlarged scale.

Referring also to FIGS. 11 and 12, a sole-and-heel structure 235 is affixed to mid-sole 232. Structure 235 comprises a generally flat, thin, elongated outer member 240, the member 240 being of one-piece, molded construction, preferably rubber. In an operative embodiment, the member had a thickness of 0.125 inch. It is essential that member 240 be highly wear resistant, since it is subject to constant engagement with the pavement. A preferred composition is made by Goodyear Tire & Rubber Company under its brand name INDY 500.

Member 240 has a sole portion 241 located under the sole of one's foot and a heel portion 242 located under the person's heel. Outer member 240 has a substantially planar interior surface 243 and an exterior surface 244 which contacts the pavement. First and second bulges 245 and 246 are molded into heel portion 242 and project downwardly from exterior surface 244. Bulges 245 and 246 respectively define cavities 245a and 246a opening to interior surface 243. In a preferred embodiment, the cavity 245a is larger than cavity 246a. A restricted passageway 247 is molded into outer member 240, between cavities 245a and 246a and opening to interior surface 243. Between surface 243 of outer member 240 and surface 233 of mid-sole 232 is adhesive 248. Outer member 240 and mid-sole 232 are thus attached, and cavities 245a and 246a are hermetically sealed, whereby air at atmospheric pressure is permanently located in the space jointly defined by cavities 245a and 246a and passageway 247.

In use, bulges 245 and 246 engage the pavement as the wearer of shoe 230 is standing. Air in cavities 245a and 246a provide a cushioning effect. In walking and jogging, bulge 245 comes in contact with the pavement first, causing air in cavity 245a to be compressed and forced through passageway 247 into cavity 246a. As heel portion 242 lifts off the pavement, air returns to cavity 245a to give a lifting effect.

In a preferred embodiment, surface 244 has a tread such as is used in athletic shoes. Although a wedge type shoe is depicted, a structure in which the forward part of the heel structure is substantially vertical can be formed.

In this embodiment, there are two heel bulges and a passageway between the two.

The basic concept is that air is used first to cushion, then to control the motion of the foot while walking, running or standing. A relatively large amount of air is moved into a smaller volume through a restricted passageway 247. Passageway 247 reduces the speed at which air moves out of main cavity 245a, thus providing cushioning. The fact that air moves from a large cavity to a small cavity 246a also provides support in the area of cavity 246a.

It is important that the small cavity 246a be pressurized from a larger air cavity 245a so that when the weight is moved by virtue of the foot being lifted for stepping, air will flow back into the larger cavity 245a in order to be ready for the next foot strike.

Large cavity 245a is for cushioning. The smaller front cavity 246a is on the medial side of the foot and will help reduce pronation, that is, the rolling of the foot to the inside.

In walking, bulge 245 strikes first, giving a cushion to the strike. Then, air is forced through passageway 247 to inner bulge 246, which prevents the foot from turning inward. The air further cushions the heel and returns outer bulge 245 as the weight is shifted forward and eventually lifted preparing the outer bulge 245 for the next strike.

Instead of heel portion being part of a heel-and-sole structure, a separate heel portion can be provided.

Because the cavity 245a is larger than cavity 246a, cavity 246a is over inflated, which then forces the air back to the cavity 245a at a faster rate. This gives the heel a slight lift during walking. Air will be forced to bulge 245 and provide a slight lift to the heel as the weight rotates forward. Cavities 245a and 246a are basically fixed in size; they do not expand any significant amount.

Figure 13:
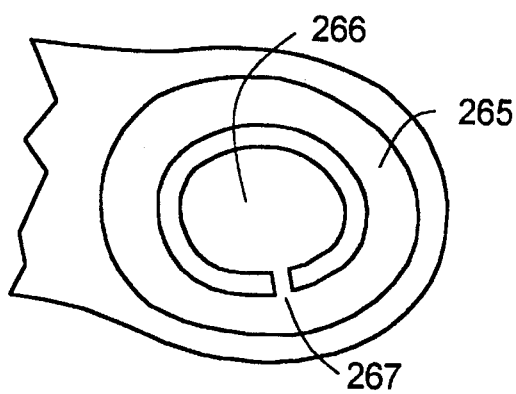
FIGS. 13–28 depict fragmentary heel portions of a shoe incorporating various embodiments of the present invention.
Figure 14:
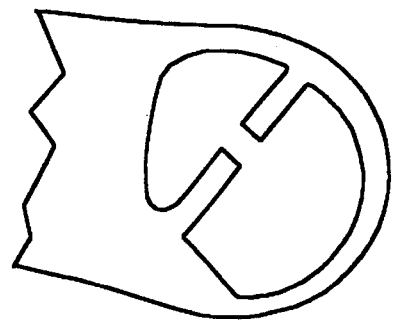
Figure 15:
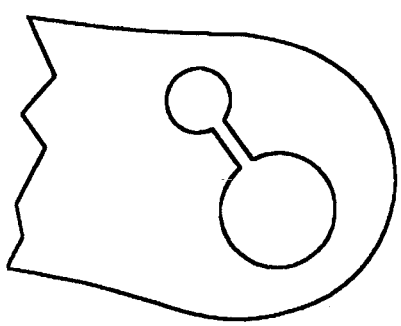
Figure 16:
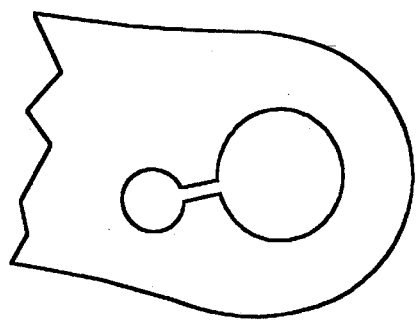

In the embodiment of FIG. 13, heel bulge 266 has a generally rounded shape and is surrounded by a toroid-shaped bulge 265 with a passageway 267 between the bulges. In this embodiment as in the rest of the embodiments, each bulge is defined by a similarly shaped cavity. Air moves back and forth between the two cavities by way of passageway 267. The embodiments in each of FIGS. 14 to 16 have two bulges in the heel portion joined by a passageway.

Figure 17:
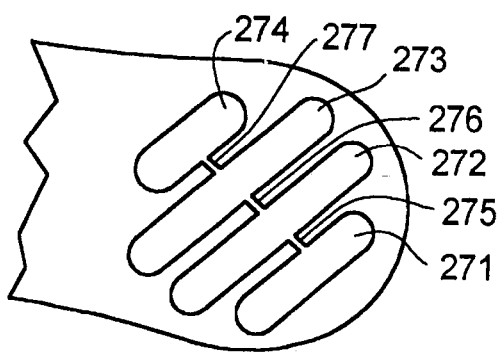
Figure 18:
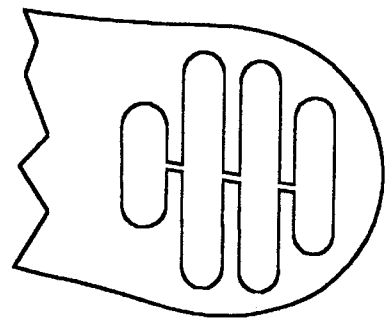

In the embodiment of FIG. 17 there are four elongated bulges 271 to 274 joined by three passageways 275 to 277 as shown. Air moves back and forth among the cavities defined by these bulges by way of such passageways. FIG. 18 depicts a similar construction, but of different orientation.

Figure 19:
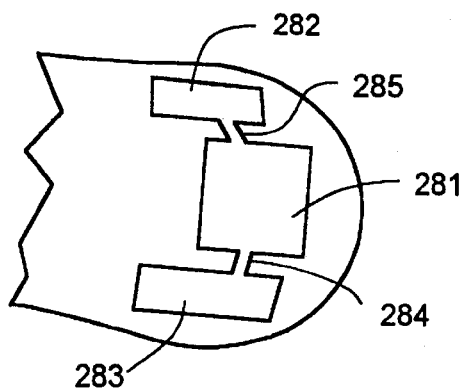

In the embodiment of FIG. 19, a larger bulge 281 is located between two smaller bulges 282 and 283. Passageway 284 connects the cavities defined by bulges 281 and 283. Passageway 285 connects the cavities defined by bulges 281 and 282. Preferably the volume of air in the cavity defined by bulge 281 is approximately the volume of combined air in the cavities defined by bulges 282 and 283.

Figure 20:
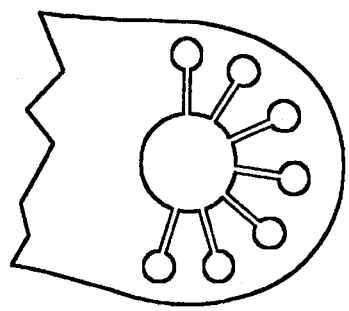
Figure 21:
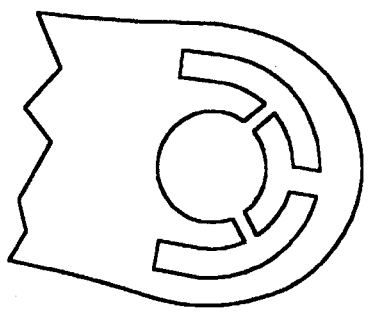
Figure 22:
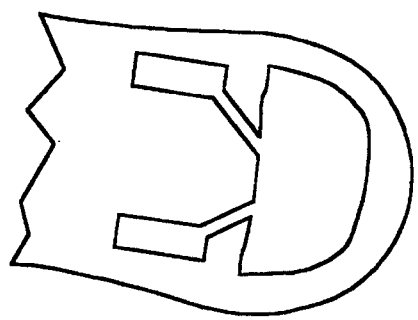
Figure 23:
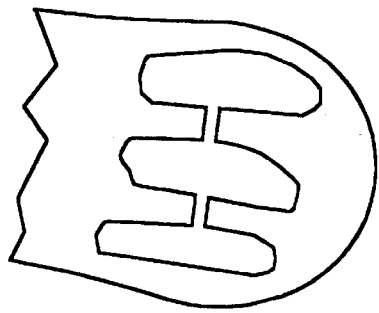
Figure 24:
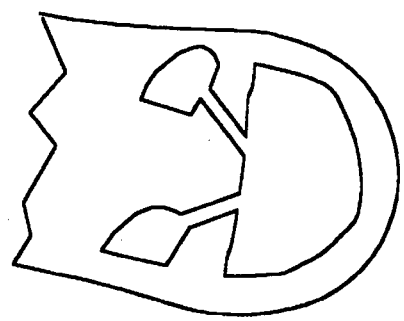

In the embodiment of FIG. 20, seven small cavities extend from one large central cavity by way of seven passageways. The embodiments of FIGS. 21, 22 and 24 are similar to the embodiment of FIG. 19 in that there is one large cavity and two smaller cavities, all under the heel connected by way of a pair of passageways. In the embodiment of FIG. 23, there are three bulges of generally the same size.

Figure 25:
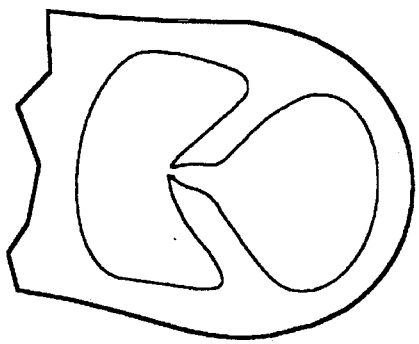
Figure 26:
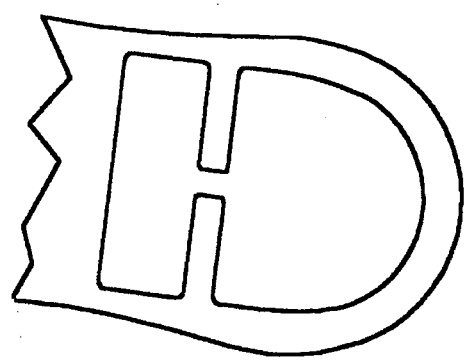
Figure 27:
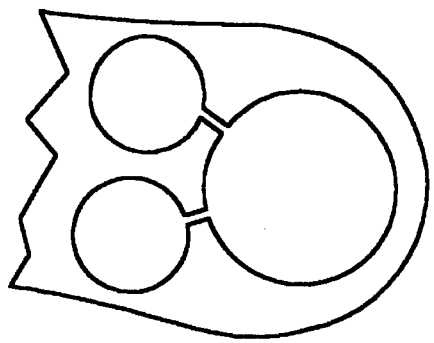
Figure 28:
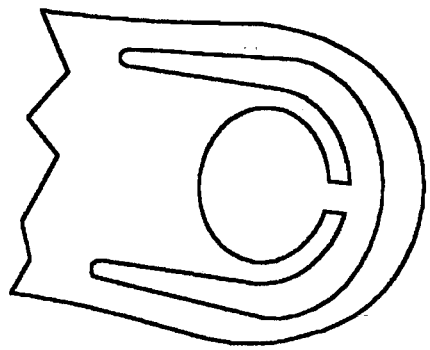

In the embodiments of FIGS. 25, 26 and 28 a pair of cavities has a pair of bulges joined by a passageway. In the embodiment of FIG. 27, two smaller bulges are connected by passageways to a larger more rearwardly located bulge.

Figure 29:
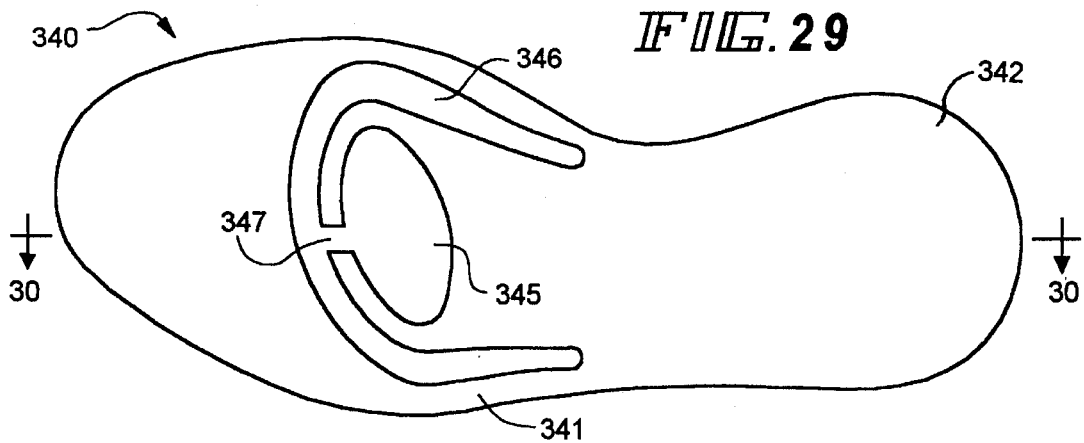
FIG. 29 is a plan view of a heel/sole structure incorporating another embodiment of the present invention.
Figure 30:
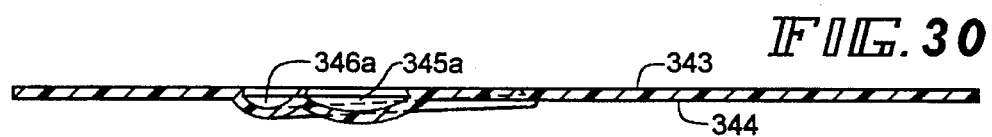
FIG. 30 is a sectional view along the line 30—30 of FIG. 29.
Figure 31:
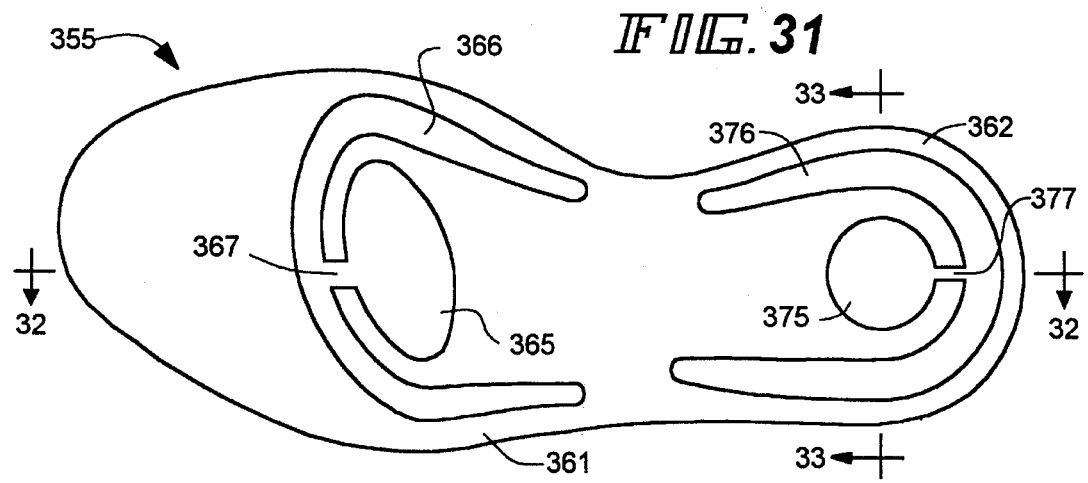
FIG. 31 is a plan view of a heel/sole structure incorporating another embodiment of the present invention.

Referring to FIGS. 29 and 30, the sole-and-heel structure depicted therein comprise a generally flat, thin, elongated outer member 340 of one-piece, molded construction, preferably rubber, like member 240.

Member 340 has a metatarsal portion 341 located under the metatarsal region of the wearer's foot and a heel portion 342 located under the person's heel. Outer member 340 has a substantially planar interior surface 343 and an exterior surface 344 which contacts the pavement. First and second bulges 345 and 346 are molded into metatarsal portion 341 and project downwardly from exterior surface 344. Bulges 345 and 346 respectively define cavities 345a and 346a opening to interior surface 343. A restricted passageway 347 is molded into outer member 340, between cavities 345a and 346a and opening to interior surface 343. A member (not shown) like member 232 is attached to surface 343 by adhesive so that cavities 345a and 346a are hermetically sealed, whereby air at atmospheric pressure is permanently located in the space jointly defined by cavities 345a and 346a and passageway 347.

In use, bulges 345 and 346 engage the pavement as the wearer of shoe 330 is standing. Air in cavities in 345a and 346a provide a cushioning effect. In walking and running, bulge 345 comes in contact with the pavement, causing air in cavity 345a to be compressed and forced through passageway 347 into cavity 346a. As metatarsal portion 341 lifts off the pavement, air returns to cavity 345a to give a lifting effect.

The design of FIGS. 29, 30 is used mainly in sports or for people with metatarsal problems. The bulges are placed to absorb the shock of impact on the metatarsal bulge from jumping or playing tennis, for example, wherein the person is more on his or her toes. The center bulge 345 absorbs the initial shock, forces the air through passageway 347 into the outer bulge 346. The air bulge 346 is compressed and acts to stabilize the foot while it is on its metatarsal and also acts as a cushion. Then, when the weight is lifted air is forced back into the center larger bulge 345 because it has been compressed into that outer horse shoe-shaped bulge 346.

In a preferred embodiment, surface 344 has a tread such as is used in athletic shoes.

The above-described embodiments are particularly desirable in a woman's high-heel shoe, in which a pad could be used on the heel portion and/or a pad could be used on the metatarsal portion.

Figure 32:
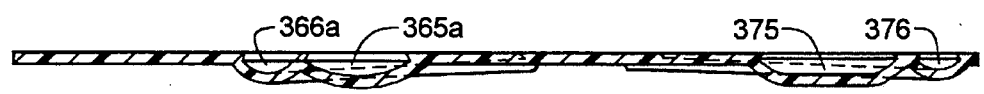
FIG. 32 is a sectional view along the line 32—32 of FIG. 31.
Figure 33:
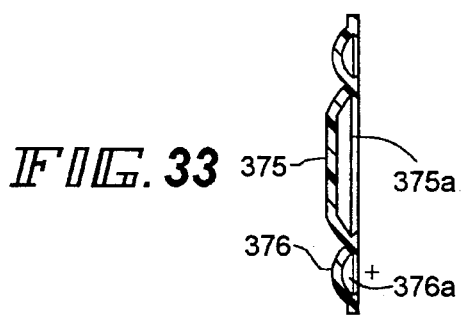
FIG. 33 is a sectional view along the line 33—33 of FIG. 31.

Yet another embodiment is depicted in FIGS. 32–33. In this embodiment, there is depicted an outer member having bulges 365, 366 and associated cavities 365a, 366a under metatarsal portion 361 (like that depicted in FIGS. 29 and 30). It also has a pair of bulges 375, 376 and associated cavities 375a, 376a under heel portion 362 (like that depicted in FIG. 28). The cavities 375a, 376a in the heel portion are joined by a passageway 377 and the cavities 365a, 366a in the metatarsal portion are joined by a passageway 367, but there is no passageway between the cavities of the metatarsal portion and the heel portion.

What has been described therefore is an improved heel and sole structure wherein there are a plurality of bulges connected by a passageway in the heel portion or in the sole portion or in both portions, but with no passageways connecting the portions.

What is claimed is:

1. A molded, one-piece resilient outer member having a heel portion and/or a metatarsal portion, the outer member having interior and exterior surfaces and having a construction to be highly wear resistant to enable said exterior surface to contact a support surface during use, a plurality of bulges molded into one of said portions and projecting from said exterior surface, said bulges respectively defining cavities opening at said interior surface, said bulges projecting from said exterior surface without the application of any elevated fluid pressure in said cavities, at least one restricted passageway molded into said outer member between said cavities and opening to said interior surface, a sealing member having a shape that matches the shape of said outer member, said sealing member being impermeable to air and having a sealing surface, and adhesive means between said sealing surface and said interior surface and said interior surface for hermetically attaching said sealing member to said outer member, whereby air at atmospheric pressure is permanently located in the space jointly defined by said passageway and said cavities, there being no passageways between said cavities and a portion other than said one portion.

2. The member of claim 1, wherein said bulges are in said heel portion and are located under the area occupied by the heel area of one's foot.

3. The member of claim 2 comprising first and second bulges defining first and second cavities and a single passageway between said cavities.

4. The member of claim 3, wherein said first bulge is forwardly of said second bulge and said first cavity is smaller than said second cavity.

5. The member of claim 1, wherein said bulges are in said metatarsal portion and are located under the area occupied by the metatarsal area of one's foot.

6. The member of claim 1, wherein said first bulge is substantially surrounded by said second bulge.

7. The member of claim 1, wherein said plurality is four and there are three passageways extending between adjacent pairs of bulges.

8. The member of claim 1, wherein said plurality is three, said one restricted passageway extending between two cavities corresponding to two of said bulges, and a further restricted passageway joining the cavities corresponding to two bulges.

* * * * *

UNITED STATES PATENT AND TRADEMARK OFFICE
CERTIFICATE OF CORRECTION

PATENT NO. : 5,545,463
DATED : August 13, 1996
INVENTOR(S) : Karl M. Schmidt et al.

It is certified that error appears in the above-indentified patent and that said Letters Patent is hereby corrected as shown below:

Column 8, lines 9, 10, delete "and said interior surface" second occurrence.

Signed and Sealed this

Seventh Day of January, 1997

Attest:

BRUCE LEHMAN

*Attesting Officer*        *Commissioner of Patents and Trademarks*